US010392320B2

(12) United States Patent
Goldman et al.

(10) Patent No.: US 10,392,320 B2
(45) Date of Patent: Aug. 27, 2019

(54) PREPARATION OF ALKYLAROMATIC COMPOUNDS

(71) Applicant: Rutgers, The State University of New Jersey, New Brunswick, NJ (US)

(72) Inventors: Alan S. Goldman, New Brunswick, NJ (US); Andrew M. Steffens, New Brunswick, NJ (US); William Schinski, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 15/580,648

(22) PCT Filed: Jun. 9, 2016

(86) PCT No.: PCT/US2016/036690
§ 371 (c)(1),
(2) Date: Dec. 7, 2017

(87) PCT Pub. No.: WO2016/201097
PCT Pub. Date: Dec. 15, 2016

(65) Prior Publication Data
US 2018/0162792 A1    Jun. 14, 2018

Related U.S. Application Data

(60) Provisional application No. 62/173,778, filed on Jun. 10, 2015.

(51) Int. Cl.
*C07C 5/41* (2006.01)
*B01J 31/24* (2006.01)
*C07C 2/42* (2006.01)
*C07C 5/52* (2006.01)

(52) U.S. Cl.
CPC ............ *C07C 5/41* (2013.01); *B01J 31/2409* (2013.01); *C07C 2/42* (2013.01); *C07C 5/52* (2013.01); *C07C 2523/24* (2013.01); *C07C 2531/24* (2013.01); *Y02P 20/52* (2015.11)

(58) Field of Classification Search
CPC ...................................................... C07C 5/41
USPC ........................................ 585/407, 418, 510
See application file for complete search history.

(56) References Cited

U.S. PATENT DOCUMENTS

| | | | | |
|---|---|---|---|---|
| 2,363,768 A * | 11/1944 | Zetterholm | ............... | C07C 5/41 585/420 |
| 2,894,046 A * | 7/1959 | Bloch | ..................... | C07C 5/412 585/421 |
| 4,034,053 A * | 7/1977 | Kaeding | .................. | B01J 29/40 585/417 |
| 4,436,946 A * | 3/1984 | Smutny | ..................... | C07C 2/14 502/175 |
| 5,304,694 A | 4/1994 | Dessau et al. | | |
| 9,302,954 B2 | 4/2016 | Goldman et al. | | |
| 2003/0105372 A1 * | 6/2003 | Feng | ......................... | C07C 5/41 585/408 |
| 2004/0158111 A1 | 8/2004 | Johnson et al. | | |
| 2011/0087000 A1 * | 4/2011 | Peters | ...................... | C07C 2/12 528/308.3 |
| 2011/0172475 A1 | 7/2011 | Peters et al. | | |
| 2013/0123552 A1 * | 5/2013 | Goldman | .................. | C07C 5/52 585/3 |
| 2014/0017744 A1 | 1/2014 | Prakash et al. | | |

FOREIGN PATENT DOCUMENTS

| | | |
|---|---|---|
| DE | 945390 C | 7/1956 |
| FR | 1380349 A | 11/1964 |
| GB | 824002 A | 11/1959 |
| WO | 2012061272 A2 | 5/2012 |
| WO | WO-2014181350 A2 * | 11/2014 ............... C07C 5/42 |

OTHER PUBLICATIONS

Herington, E. F. G. et. al. "On the catalytic cyclization of aliphatic hydrocarbons. II"; Proc. Royal. Soc. A., (1945); pp. 447-463. (Year: 1945).*
Ahuja, et al., "Catalytic dehydroaromatization of n-alkanes by pincer-ligated iridium complexes", Nature Chemistry 3 (2), 167-171 (2011).
Al-Jarallah, et al., "Ethylene dimerization and oligomerization to butene-1 and linear α-olefins: A review of catalytic systems and processes", Catal Today 14(1), 1-121 (1992).
Al-Sa'Doun, "Dimerization of ethylene to butene-1 catalyzed by Ti(OR')4-AIR3", Applied Catalysis A: General 105(1), 1-40 (1993).
Choi, et al., "Dehydrogenation and related reactions catalyzed by iridium pincer complexes", Chem Rev 111, 1761-1779 (2011).
Dittmeyer, et al., "Membrane reactors for hydrogenation and dehydrogenation processes based on supported palladium", J Mol Catal A: Chem 173, 135-184 (2001).
Huang, et al., "Efficient Heterogeneous Dual Catalyst Systems for Alkane Metathesis", Adv Synth Catal 352, 125-135 (2010).
Huang, et al., "Highly Active and Recyclable Heterogeneous Iridium Pincer Catalysts for Transfer Dehydrogenation of Alkanes", Adv Synth Catal 351, 188-206 (2009).
Huang, et al., "Ligand exchanges and selective catalytic hydrogenation in molecular single crystals", Nature 465, 598-601 (2010).
Kagan, et al., "Catalytic asymmetric Diels Alder reactions", Chemical Reviews 92, 1007-1019 (1992).
Karinen, et al., "Catalytic synthesis of a novel tertiary ether, 3-methoxy-3-methyl heptane, from 1-butene", J Mol Catal A: Chem 152, 253-255 (2000).
Liu, et al., "Efficient thermochemical alkane dehydrogenation and isomerization catalyzed by an iridium pincer complex", Chem Commun 655-656 (1999).

(Continued)

*Primary Examiner* — Philip Y Louie

(74) *Attorney, Agent, or Firm* — Viksnins Harris Padys Malen LLP

(57) ABSTRACT

Described herein are methods useful for preparing alkylaromatics.

20 Claims, No Drawings

(56) References Cited

OTHER PUBLICATIONS

Okuhara, "Water-Tolerant Solid Acid Catalysts", Chemical Reviews 102, 3641-3665 (2002).
Paglieri, et al., "Innovations in Pd Membrane Research", Purif Methods 31, 1-169 (2002).
Patent Cooperation Treaty, International Searching Authority, Search Report and Written Opinion for PCT/US2016/036690, 11 pages, dated Sep. 7, 2016.
Rosi, et al., "Hydrogen Storage in Microporous Metal-Organic Frameworks", Science 300, 1127-1129 (2003).
Sakamoto, et al., Ber Bunsen-Ges Phys Chem Chem Phys 99, 807-820 (1995).
Smieskova, et al., "Aromatization of light alkanes over ZSM-5 catalysts: Influence of the particle properties of the zeolite", Applied Catalysis A: General 268, 235 (2004).
Von Koten, et al., "Periphery-functionalized organometallic dendrimers for homogeneous catalysis", J Mol Catal A: Chem 146, 317-323 (1999).
Zhang, et al., "Dimerization of 1-butene via zirconium-based Ziegler-Natta catalyst", Catalysis Letters 64(2-4), 147-150 (2000).

* cited by examiner

PREPARATION OF ALKYLAROMATIC COMPOUNDS

CROSS REFERENCE TO RELATED APPLICATION

This application claims the benefit of priority of U.S. Provisional application Ser. No. 62/173,778, filed Jun. 10, 2015, which application is herein incorporated by reference.

STATEMENT OF GOVERNMENT SUPPORT

This invention was made with government support under CHE-0650456 awarded by the National Science Foundation. The government has certain rights in the invention.

BACKGROUND p-Xylene is an extremely important chemical building block and is used in a variety of applications, but particularly as a starting material for the ubiquitous polymer polyethylene terephthalate or "polyester" (Köpnick, H., et al., 2000. Polyesters. Ullmann's Encyclopedia of Industrial Chemistry. Wiley-VCH Verlag GmbH & Co. KGaA, 2002). Accordingly, there is a need to develop new or less expensive ways to prepare xylene (e.g., p-xylene) or methods to prepare p-xylene from alternative starting materials.

SUMMARY OF CERTAIN EMBODIMENTS OF THE INVENTION

Compounds including butenes can be utilized as a starting material to synthesize p-xylene through the intermediate 3-methyleneheptane or 3-methylheptane. Accordingly, one embodiment provides a method of preparing p-xylene, comprising converting 3-methyleneheptane or 3-methylheptane to p-xylene. Since 3-methyleneheptane (also known as 2-ethyl-1-hexene or 2-butyl-1-butene) is readily accessible from dimerization of butenes (e.g., 1-butene, 2-butene and mixtures thereof), this represents a route to p-xylene from butenes. Since butenes can be readily prepared from ethylene, the methods described herein represent a route to p-xylene from ethylene. Butenes are also accessible from a variety of sources including the cracking of petroleum and the dehydrogenation of butane.

One embodiment provides a method of preparing p-xylene, comprising converting 3-methyleneheptane to p-xylene. One embodiment provides a method of preparing p-xylene, comprising converting 3-methylheptane to p-xylene. Accordingly, one embodiment provides a method of preparing p-xylene, comprising converting 3-methyleneheptane or 3-methylheptane or a mixture thereof to p-xylene. One embodiment provides a method of preparing p-xylene, comprising converting 1-butene to p-xylene. One embodiment provides a method of preparing p-xylene, comprising converting 2-butene to p-xylene. One embodiment provides a method of preparing p-xylene, comprising converting 1-butene or 2-butene or a mixture thereof to p-xylene.

DETAILED DESCRIPTION

It has been discovered that ethylene, via butenes, can be utilized as a starting material to synthesize p-xylene through the intermediate 3-methyleneheptane or 3-methylheptane. This is especially important as ethylene is quite inexpensive due to the abundance of ethane precursor from shale gas. Alternatively, butenes from any other sources can be utilized as starting material. For example, this process could be easily integrated within existing industrial plants using Fluidized Catalytic Cracking (FCC) which produces butenes. This process is also important as in some embodiments it selectively (e.g., in greater ratio) produces p-xylene over other products (e.g., ethyl benzene, o-xylene and dimers) including other regioisomers of xylene (e.g., o-xylene). In one embodiment o-xylene is produced by the process described herein. O-xylene obtained by the process described herein can be converted to p-xylene by a conventional p-xylene unit. In one embodiment ethylbenzene is produced by the process described herein. Ethylbenzene obtained by the processes described herein can be converted to styrene. The conversion of ethylene to p-xylene is illustrated in Scheme I.

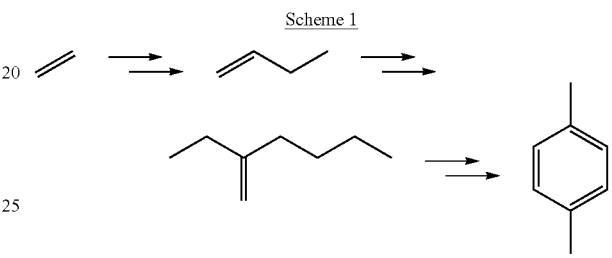

Scheme 1

As indicated in Scheme 1, ethylene can be dimerized to form 1-butene (Köpnick, H., et al., 2000. Polyesters. Ullmann's Encyclopedia of Industrial Chemistry. Wiley-VCH Verlag GmbH & Co. KGaA; Al-Sa'doun, A. W. Applied Catalysis A: General, 1993; 105 (1), 1-40., Al-Jarallah, A. M et al., Catal. Today, 1992, 14 (1), 1-121.) 1-Butene can then be dimerized to 3-methyleneheptane (Zhang, W. Li, et al., Catalysis Letters, 2000, 64, 147-150; Karinen, R. S., et al., J. Mol. Catal. A: Chem, 2000, 152, 253). Similarly, 2-butene can also be dimerized to form 3-methyleneheptane as the major product (Goddard, R. E., et al., Dimerization of olefins. GB 824002, Nov. 25, 1959; Ziegler, K., et al., 2-Ethyl-1-hexene. DE 945390, Jul. 5, 1956; Endler, H., et al., Dimerizing monoolefins. FR 1380349, Nov. 27, 1964). As shown herein, 3-methyleneheptane (or 3-methylheptane) can be dehydroaromatized to give p-xylene.

Reagents that Facilitate Dehydroaromatization (e.g., Catalysts).

The dehydroaromatization reactions described herein (e.g., reactions for preparing p-xylene) are generally conducted in the presence of a reagent to facilitate (e.g., catalyze) the reaction. In one embodiment the dehydroaromatization reaction is conducted in the presence of a catalyst. The catalyst can be any reagent that is used to convert the starting material used in the dehydroaromatization reaction to a product (e.g., p-xylene). In one embodiment the catalyst is used in a sub-stoichiometric amount when compared to starting material. In one embodiment the catalyst is a metal catalyst. In one embodiment the catalyst is a transition metal catalyst (the catalyst comprises a transition metal). In one embodiment the catalyst is an iridium catalyst (the catalyst comprises iridium).

There are many pincer catalysts and other potential catalysts that may be useful for the methods described herein. (van Koten et al., J. Mol. Catal. A: Chem. 146, 317-323 (1999); The Chemistry of Pincer Compounds; Morales-Morales, D.; Jensen, C., Eds.; Elsevier: Amsterdam, 2007). The US patent application 2013/0123552 A1 and the PCT application WO2012/061272 also describe catalysts including pincer catalysts. The content of each of these documents, and in particular the catalysts describer therein are hereby incorporated by reference. Accordingly, in one embodiment the catalyst is a pincer-ligated metal catalyst e.g., complex). In one embodiment the catalyst is a pincer-ligated transition metal catalyst. In one embodiment the catalyst is a pincer-ligated iridium catalyst. In one embodiment the catalyst is a pincer-ligated iridium complex. In one embodiment the catalyst comprises a pincer-ligated iridium complex. In one embodiment the catalyst comprises a pincer-ligated iridium complex in solution. Many such pincer complexes, however, are also well known to be effective dehydrogenation catalysts when supported on solid surfaces as well as in solution (Huang, Z. et al., Adv. Synth. Catal. 351, 188-206 (2009); Huang, Z. et al., Adv. Synth. Catal. 352, 125-135 (2010)) which document is hereby incorporated by reference in its entirety. In one embodiment the catalyst precursor is ($^{iPr4}$PCOP)Ir(H)(Cl) or ($^{iPr4}$PCOP)Ir(H)(Cl). In one embodiment the catalyst precursor comprises ($^{iPr4}$PCOP)Ir(H)(Cl) or ($^{iPr4}$PCOP)Ir(H)(Cl) and base. Other metal catalysts may be used including other derivatives of the ($^{iPr}$PCP)Ir and ($^{iPr4}$PCOP)Ir groups and other pincer-ligated iridium complexes.

In one embodiment the metal catalyst further comprises additional atoms associated (e.g., bonded, coordinated) with the metal. The additional atoms can be for example ligands that are associated with the metal. In one embodiment the catalyst is a soluble catalyst such as a soluble metal catalyst. In one embodiment the catalyst is a homogeneous catalyst (e.g., a soluble metal catalyst). Heterogeneous catalysts are also known to perform dehydroaromatization reactions similar to homogeneous catalysts (Smiešková, A., et al., *Applied Catalysis A: General* 2004, 268, 235). In one embodiment the catalyst is a heterogeneous catalyst. In one embodiment the catalyst is an insoluble catalyst (e.g., partially or completely insoluble). In one embodiment the catalyst is supported on a solid surface. It is to be understood that the term "catalyst(s)" as used herein includes all forms of the catalyst including pre-catalyst forms of a catalyst which provide the corresponding active form of the catalyst (e.g., an active catalyst).

Hydrogen Acceptors.

Hydrogen acceptors are compounds that facilitate the dehydroaromatization reactions described herein by facilitating the removal of hydrogen formed during the reaction. Hydrogen acceptors used herein include t-butylethylene (TBE). It is known that pincer-ligated iridium complexes can be used to effect alkane dehydrogenation and dehydroaromatization using many hydrogen acceptors other than TBE (Zhang, W., et al., *Catalysis Letters,* 2000, 64, 147-150). Accordingly, other hydrogen acceptors may be useful in the dehydroaromatization reactions described herein.

Acceptorless Systems (Dehydroaromatization Reactions in the Absence of a Hydrogen Acceptor).

Dehydrogenation can be effected by catalysts without the use of any sacrificial acceptor ("acceptorless dehydrogenation") (Choi, J.; et al., Chem. Rev. 2011, 111, 1761-1779; Liu, F.; et al., Chem. Commun. 1999, 655-656). Accordingly, "acceptorless" systems (systems without a hydrogen acceptor in which hydrogen is released) may be useful in the dehydroaromatization methods described herein. Other methods to remove hydrogen which are not based on acceptors may be used and may involve refluxing or a physical method (e.g., bubbling inert gas through the system) to remove hydrogen. Hydrogen sponges (materials or molecules that absorb hydrogen reversibly) or hydrogen-permeable membranes (e.g., palladium) may also be used. Possible hydrogen sponges include MOF's (metal-organic-frameworks), Rosi et al., Science 300, 1127-1129 (2003)), palladium metal or metal alloys, (Sakamoto et al., Ber. Bunsen-Ges. Phys. Chem. Chem. Phys. 99, 807-820 (1995)), crystalline pincer complexes. (Huang et al., Nature 465, 598-601 (2010). These or other such materials may be recycled after absorbing hydrogen. Hydrogen-permeable membranes are known in the art. (Paglieri et al., Purif. Methods 31, 1-169 (2002); Dittmeyer et al., J. Mol. Catal. A-Chem. 173, 135-184 (2001)).

Co-Catalysts

Co-catalysts may also be used in the methods provided herein. In particular, co-catalysts for dehydroaromatization reactions may be used. Addition of a cyclization co-catalyst may promote the overall reaction rates and/or yields; for example, it is known that Lewis acid catalysts may be used to catalyze electrocyclization reactions. (Kagan et al., Chemical Reviews 92, 1007-1019 (1992); Okuhara, Chemical Reviews 102, 3641-3665 (2002)).

It is to be understood that the embodiments described below are non-limiting and that two or more embodiments may be combined.

One embodiment provides a method of preparing p-xylene, comprising converting 3-methyleneheptane or 3-methylheptane to p-xylene. One embodiment provides a method of preparing p-xylene, comprising converting 3-methyleneheptane to p-xylene. One embodiment provides a method of preparing p-xylene, comprising converting 3-methylheptane to p-xylene. One embodiment provides a method of preparing p-xylene, comprising converting 3-methyleneheptane or 3-methylheptane or a mixture thereof to p-xylene.

One embodiment provides a method of preparing p-xylene, comprising converting 1-butene or 2-butene to p-xylene. One embodiment provides a method of preparing p-xylene, comprising converting 1-butene or 2-butene or a mixture thereof to p-xylene. One embodiment provides a method of preparing p-xylene, comprising converting 1-butene to p-xylene. One embodiment provides a method of preparing p-xylene, comprising converting 2-butene to p-xylene. In one embodiment the method is characterized in that the conversion comprises the use of a catalyst. In one embodiment the method is characterized in that the 1-butene or 2-butene is first converted to an intermediate compound (e.g., 3-methyleneheptane) which intermediate is contacted with a catalyst. In one embodiment the method is characterized in that the 1-butene is first converted to an intermediate compound (e.g., 3-methyleneheptane) which intermediate is contacted with a catalyst. In one embodiment the method is characterized in that the 2-butene is first converted to an intermediate compound (e.g., 3-methyleneheptane) which intermediate is contacted with a catalyst. In one embodiment the method is characterized in that the 1-butene or 2-butene or a mixture thereof is first converted to an intermediate compound (e.g., 3-methyleneheptane or 3-methylheptane or a mixture thereof) which intermediate is contacted with a catalyst.

One embodiment provides a method of preparing p-xylene, comprising converting ethylene to p-xylene. In one embodiment the method is characterized in that the conversion comprises the use of a catalyst. In one embodiment the method is characterized in that the ethylene is first converted to an intermediate compound (e.g., 3-methyleneheptane) which intermediate is contacted with a catalyst.

In one embodiment the 3-methyleneheptane or 3-methylheptane is contacted with a catalyst.

In one embodiment the catalyst is a metal catalyst.

In one embodiment the catalyst is a transition metal catalyst.

In one embodiment the catalyst is an iridium catalyst.

In one embodiment the catalyst is a pincer-ligated catalyst.

In one embodiment the catalyst is a homogeneous catalyst (e.g., the catalyst is uniformly mixed in the reaction media such as being soluble in the reaction media).

In one embodiment the catalyst is a heterogeneous catalyst (e.g., the catalyst is not uniformly mixed in the reaction media such as being insoluble (such as partially or completely) in the reaction media).

In one embodiment the catalyst is $(^{iPr4}\text{PCOP})\text{Ir}$ or $(^{iPr4}\text{PCP})\text{Ir}$.

In one embodiment the catalysts $(^{iPr4}\text{PCOP})\text{Ir}$ and $(^{iPr4}\text{PCP})\text{Ir}$ are derived from the corresponding catalyst precursors $(^{iPr4}\text{PCOP})\text{Ir}(\text{H})(\text{Cl})$ and $(^{iPr4}\text{PCP})\text{Ir}(\text{C}_2\text{H}_4)$.

In one embodiment the step of contacting 3-methyleneheptane or 3-methylheptane with the catalyst is performed in the presence of an H-acceptor.

In one embodiment the H-acceptor is t-butylethylene (TBE).

In one embodiment the conversion is performed above 170° C.

In one embodiment the conversion is performed at about 200° C.

In one embodiment the conversion is performed in a solvent.

In one embodiment the solvent is an aromatic hydrocarbon solvent.

In one embodiment the solvent is mesitylene.

In one embodiment the 3-methyleneheptane or 3-methylheptane is less than or about 0.50 M in the solvent.

One embodiment provides a composition comprising 3-methyleneheptane or 3-methylheptane or a mixture thereof and a catalyst.

One embodiment provides a composition comprising 1-butene or 2-butene or a mixture thereof and a catalyst.

Certain embodiments of the invention will now be illustrated by the following non-limiting Example.

EXAMPLE 1

Dehydroaromatization of 3-methyleneheptane

The dehydroaromatization of 3-methyleneheptane yields multiple products. The products include p-xylene, o-xylene, ethylbenzene, and a variety of unidentified compounds including dimers due to Diels-Alder reactions. Scheme 2 shows the conditions of a representative test reaction using tert-butyl ethylene (TBE) as a hydrogen acceptor. Scheme 3 shows the catalyst precursors used in the dehydroaromatization reaction. Table 1 shows the concentration of the products after dehydroaromatization and percent conversion for reactions with varying conditions.

Scheme 2

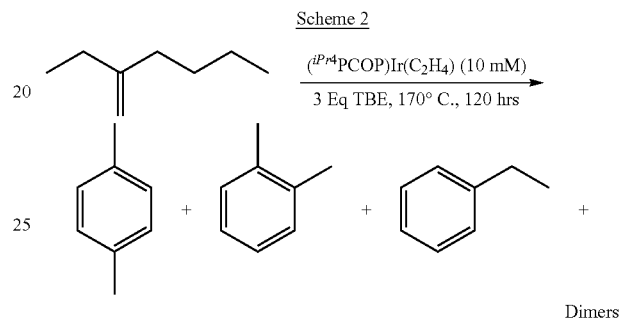

Scheme 3

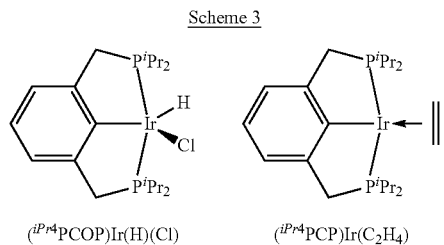

$(^{iPr4}\text{PCOP})\text{Ir}(\text{H})(\text{Cl})$      $(^{iPr4}\text{PCP})\text{Ir}(\text{C}_2\text{H}_4)$

TABLE 1

Concentrations of Products after Dehydroaromatization and Conversions

| Conditions (10 mM catalyst) | Ethylbenzene/mM (% yield) | o-Xylene/mM (% yield) | p-Xylene/mM (% yield) | Dimers/mM (% yield) |
|---|---|---|---|---|
| $(^{iPr4}\text{PCOP})\text{Ir}(\text{H})(\text{Cl})$ at 170° C. 1.8M 3-methyleneheptane 5.45M TBE 30 mM NaOtBu, 120 hours | 40 (2%) | 130 (7%) | 680 (38%) | 400 (44%) |
| $(^{iPr4}\text{PCOP})\text{Ir}(\text{H})(\text{Cl})$ at 200° C. 1.8M 3-methyleneheptane 5.45M TBE 30 mM NaOtBu, 120 hours | 100 (6%) | 130 (7%) | 910 (51%) | 300 (33%) |
| $(^{iPr4}\text{PCP})\text{Ir}(\text{C}_2\text{H}_4)$ at 170° C. 1.8M 3-methyleneheptane 5.45M TBE 20 mM NaOtBu, 120 hours | 25 (1%) | 160 (9%) | 850 (47%) | 325 (36%) |
| $(^{iPr4}\text{PCOP})\text{Ir}(\text{HCl})$ at 170° C. 0.36M 3-methyleneheptane 1.09M TBE 30 mM NaOtBu, 120 hours Reaction diluted 80% in mesitylene | 15 (4%) | 40 (11%) | 200 (55%) | 45 (25%) |
| $(^{iPr4}\text{PCP})\text{Ir}(\text{HCl})$ at 200° C. 0.24M 3-methyleneheptane 1.09M TBE 30 mM NaOtBu, 120 hours Reaction diluted 80% in mesitylene | 15 (7%) | 30 (11%) | 140 (53%) | 25 (18%) |

TABLE 1-continued

Concentrations of Products after Dehydroaromatization and Conversions

| Conditions (10 mM catalyst) | Ethylbenzene/mM (% yield) | o-Xylene/mM (% yield) | p-Xylene/mM (% yield) | Dimers/mM (% yield) |
|---|---|---|---|---|
| ($^{iPr4}$PCOP)Ir(HCl) at 200° C. 0.25M 3-methyleneheptane 1.09M TBE 30 mM NaOtBu, 120 hours Reaction diluted 80% in mesitylene | 20 (7%) | 30 (11%) | 165 (60%) | 30 (20%) |

Entry 1 shows yields from a typical dehydroaromatization reaction, entry 2 shows good yields due to increased temperature, entry 3 shows that the ($^{iPr4}$PCP)Ir(C$_2$H$_4$) catalyst works very well for this reaction, entry 4 shows that dilution with mesitylene gives good yields of p-xylene while lowering dimer formation, entry 5 shows the lowest amount of dimers formed and entry 6 shows the best yield of p-xylene.

All publications cited herein are incorporated herein by reference. While in this application certain embodiments of invention have been described, and many details have been set forth for purposes of illustration, it will be apparent to those skilled in the art that certain of the details described herein may be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not pose a limitation on the scope of the invention unless otherwise specifically recited in the claims. No language in the specification should be construed as indicating that any non-claimed element as essential to the practice of the invention.

What is claimed is:

1. A method of preparing p-xylene, comprising converting 3-methyleneheptane to p-xylene wherein the 3-methyleneheptane is contacted with an iridium catalyst.

2. A method of preparing p-xylene, comprising converting 3-methyleneheptane or 3-methylheptane to p-xylene wherein the 3-methyleneheptane or 3-methylheptane is contacted with a pincer-ligated catalyst.

3. The method of claim 2, wherein the catalyst is a transition metal catalyst.

4. The method of claim 2, wherein the catalyst is an iridium catalyst.

5. The method of claim 2, wherein the catalyst is ($^{iPr4}$PCOP)Ir or ($^{iPr4}$PCP)Ir.

6. The method of claim 2, wherein the step of contacting 3-methyleneheptane or 3-methylheptane with the catalyst is performed in the presence of an H-acceptor.

7. The method of claim 1, wherein the catalyst is a pincer-ligated catalyst.

8. The method of claim 1, wherein the conversion is performed in a solvent.

9. The method of claim 1, wherein the p-xylene is obtained in greater than 30% yield.

10. The method of claim 1, wherein the p-xylene is obtained in greater than 50% yield.

11. The method of claim 1, wherein the p-xylene is isolated from other compounds which are formed in addition to the p-xylene.

12. The method of claim 1, wherein the p-xylene is purified to remove at least a portion of one or more compounds formed in addition to the p-xylene.

13. The method of claim 1, wherein the iridium catalyst is ($^{iPr4}$PCOP)Ir or ($^{iPr4}$PCP)Ir.

14. The method of claim 1, wherein the step of contacting 3-methyleneheptane with the iridium catalyst is performed in the presence of an H-acceptor.

15. The method of claim 14, wherein the H-acceptor is t-butylethylene (TBE).

16. A method of preparing p-xylene, comprising converting 3-methyleneheptane or 3-methylheptane to p-xylene, wherein the 3-methyleneheptane or 3-methylheptane is contacted with catalyst wherein the step of contacting 3-methyleneheptane or 3-methylheptane with the catalyst is performed in the presence of an H-acceptor, wherein the H-acceptor is t-butylethylene (TBE).

17. A method of preparing p-xylene, comprising converting 1-butene or 2-butene or a mixture thereof to p-xylene, characterized in that the 1-butene or 2-butene or a mixture thereof is first converted to an intermediate that is 3-methyleneheptane or 3-methylheptane, wherein the intermediate is contacted with a pincer-ligated catalyst to prepare the p-xylene.

18. The method of claim 17, wherein the pincer-ligated catalyst is a pincer-ligated transition metal catalyst.

19. The method of claim 17, wherein the pincer-ligated catalyst is a pincer-ligated iridium catalyst.

20. A method of preparing p-xylene, comprising converting 1-butene or 2-butene or a mixture thereof to p-xylene, characterized in that the 1-butene or 2-butene or a mixture thereof is first converted to an intermediate that is 3-methyleneheptane or 3-methylheptane, wherein the intermediate is contacted with a catalyst to prepare the p-xylene, wherein the catalyst is any species containing the unit ($^{iPr4}$PCOP)Ir or ($^{iPr4}$PCP)Ir or other pincer-ligated iridium species.

\* \* \* \* \*